United States Patent [19]
Hu et al.

[11] Patent Number: 5,409,833
[45] Date of Patent: Apr. 25, 1995

[54] MICROVESSEL CELL ISOLATION APPARATUS

[75] Inventors: Can B. Hu, Irvine; Minh T. Ma, Santa Ana; Than Nguyen, Huntington Beach; Richard Rhee, Diamond Bar; Keith Myers, El Toro, all of Calif.

[73] Assignee: Baxter International Inc., Deerfield, Ill.

[21] Appl. No.: 86,778

[22] Filed: Jul. 1, 1993

[51] Int. Cl.⁶ .............................. C12M 1/42
[52] U.S. Cl. .................... 435/288; 435/311; 422/101; 422/102; 422/104; 494/36
[58] Field of Search ............... 435/1, 262, 267, 271, 435/284–286, 288, 296, 311, 802, 809, 316; 422/99, 101, 102, 103, 104; 494/16, 36

[56] References Cited

U.S. PATENT DOCUMENTS

| | | | |
|---|---|---|---|
| 2,910,406 | 10/1959 | Novak . | |
| 4,423,145 | 12/1983 | Stampfer et al. | 435/32 |
| 4,670,394 | 6/1987 | Pollard et al. | 435/68 |
| 4,981,596 | 1/1991 | Shiino et al. | 210/650 |
| 5,035,708 | 7/1991 | Alchas et al. | 623/1 |
| 5,038,958 | 8/1991 | Dreier | 422/102 |

FOREIGN PATENT DOCUMENTS 0446450 9/1991 European Pat. Off. .......... 435/284
0512769 11/1992 European Pat. Off. .

OTHER PUBLICATIONS

Ace Scientific Supply Co., Inc. E. Brunswich, N.J. 1983 Catalog pp. 557–559.

*Primary Examiner*—William H. Beisner
*Attorney, Agent, or Firm*—Poms Smith Lande Rose Raymond Sun

[57] ABSTRACT

A processing vessel for isolating microvessel endothelial cells from liposuctioned fat tissues includes a fat-receiving basket defined by polyester screen material. Fat tissue removed from a patient by liposuction is received into the basket and is rinsed and digested with an enzymatic solution. The freed microvessel endothelial cells from the fat tissues are separated from the fat cells, and from blood cells and other materials which may be present in the basket by centrifuging. A bottom chamber of the processing vessel is configured to define a "pellet" of isolated endothelial cells which may be removed from the processing vessel for deposition on the inner lumenal surface of a synthetic graft which the fat-donor patient is to receive.

31 Claims, 3 Drawing Sheets

MICROVESSEL CELL ISOLATION APPARATUS

BACKGROUND OF THE INVENTION

1. Field of the Invention

The present invention is in the field of vascular grafting. More particularly, the present invention relates to methods and apparatus for isolation of microvessel cells, generally referred to as endothelial cells, from a patient who is to receive a synthetic graft which has an inner lumenal surface. The microvessel cells are deposited on this inner lumenal surface of the graft.

2. Related Technology

A conventional technology for treating a synthetic or naturally occurring surface with microvessel endothelial cells is set forth in U.S. Pat. No. 4,820,626, issued 11 Apr. 1989 to Stuart K. Williams, et al. In summary, the teaching of this Williams patent is to obtain tissues rich in microvessel endothelial cells, to separate the endothelial cells from the other tissues, and to place these cells onto the inner lumenal surface of the graft.

Recently, technologies for the harvesting, separation, isolation, culturing, and deposition onto a synthetic vascular graft of microvessel endothelial cells have progressed somewhat beyond the labor and skill intensive laboratory methods initially used. Consequently, the time consuming methods which were initially used to prove the efficacy of this technology for reducing the thrombogenicity of synthetic vascular grafts are now practiced with apparatus making the procedure less time consuming, less prone to error, more sterile, and safer for the patient and medical personnel.

Further to the above, a conventional apparatus and method for preparing a synthetic vascular graft with a lumenal lining of endothelial cells taken by liposuction from the patient who is to receive the graft is known in accord with U.S. Pat. No. 5,035,708, issued 30 Jul. 1991, to Paul G. Alchas, et al. According to the Alchas patent, an endothelial cell isolation device includes a primary chamber tapering downwardly to a secondary chamber or ampule. The secondary chamber also has an upper inlet port and a lower outlet port communicating outwardly of the cell isolation device. Digested fat tissue slurry, with microvessel endothelial cells therein, is introduced into the upper primary chamber, and the isolation device is centrifuged at about 700 G for about 7 minutes to produce an endothelial cell product in the form of a "pellet" composed essentially of endothelial cells. This pellet of endothelial cells is then isolated from the fat cells and red blood cells also in the chamber of the isolation device, and is transferred from the cell isolation device to a cell deposition apparatus. This cell deposition apparatus effects dispersal of the endothelial cells in a solution of autologous serum and media. From this suspension, the endothelial cells are deposited on the inner lumenal surface of a synthetic vascular graft.

However, with a cell isolation device of the type taught by the Alchas patent, the relative inefficiency of washing of the slurry to remove free fat therefrom, in combination with the inefficiency of separation of the microvessel endothelial cells from the fat cells in the slurry means that a low yield of endothelial cells is provided with which to do the cell deposition onto the synthetic graft. As a result, many microvessel endothelial cells which are present in the fat slurry are simply not recovered and are thrown away with the disposable device. Consequently, the patient may have to endure a more extensive liposuction than otherwise would be required in order to provide a sufficient number of endothelial cells.

Yet another conventional apparatus for isolating the microvessel endothelial cells present in a fat slurry is known in accord with European Patent Application No. 92303973.9, having a Publication No. 512,769, and a publication date of Nov. 11, 1992. According to the identified publication, a singular processing vessel is utilized to receive fat removed from a patient by liposuction, to rinse this fat, to digest the fat product in order to free the microvessel endothelial cells, and to isolate these endothelial cells from the fat cells and other materials present in the vessel. The endothelial cells so isolated are then transferred from the processing vessel to a graft deposition device for deposition on the inner lumenal surface of the synthetic graft. The conventional teaching is to employ a metallic screen partition or screen basket to define a fat-receiving and rinsing chamber. However, as is explained below, it appears as if the surface energy or electro-chemical activity of the metallic mesh screen material is itself detrimental to microvessel cells.

However, a need exists to improve the yield of viable endothelial cells recovered from a fat specimen taken from a patient preparatory to implantation of a synthetic graft. That is, the endothelial cells which are present in the fat specimen should be more efficiently separated from the fat cells, blood cells, connective tissues, and other materials which are present in the specimen, so that a larger number of such endothelial cells are available to be deposited onto the synthetic graft.

Additionally, a need exists to improve the safety, efficiency in terms of time and skills required and in terms of yield of microvessel cells available for deposition on the graft, manufacturability, and user convenience of the available apparatus for separating, and isolating endothelial microvessel cells for use on the vascular graft. In other words, the entire procedure should be made less of a laboratory-like procedure requiring highly skilled personnel, make-shift apparatus, and considerable time delays; and into a procedure which can be accomplished with little specialized training, in a short time while the graft implantation surgery is underway, and with high sterility and safety for both the patient and the surgical personnel.

SUMMARY OF THE INVENTION

In view of the deficiencies of the related technology as outlined above, a primary object for this invention is to improve the yield or recovery rate of viable microvessel endothelial cells from digested fat slurry preparatory to deposition of these cells on a synthetic vascular graft.

Another object for the present invention is to improve the manufacturability of an endothelial cell isolation apparatus for use in isolating microvessel endothelial cells as outlined above.

Still another object for the present invention is to improve the protection afforded to medical personnel with respect to avoiding exposure to blood-borne infectious agents;

Another objective of the present invention is to improve the ease of manufacture for a process vessel portion of the apparatus by facilitating injection molding of this process vessel portion.

Yet another objective of the present invention is to improve the washing effectiveness of liposuctioned fat removed from a patient who is to receive a graft lined with microvessel cells from the fat.

Still another object for this invention is to provide a processing vessel configured to receive liposuctioned fat tissues, for effectively rinsing these fat tissues to remove undesired constituents, for digesting the fat tissues to a slurry having freed microvessel cells therein, for separating the microvessel cells in response to centrifuging of the fat slurry, and providing for separation of the separated microvessel cells for further processing on the vascular graft with minimized loss of the separated cells.

Accordingly, the present invention provides a process vessel for use in receiving, cleansing, digesting and isolating microvessel cells from adipose tissue. This process vessel defines a process chamber and includes a screen basket which substantially fills the process chamber for receiving the adipose tissue.

Particularly, the present invention provides a process vessel of the above-described type in which the screen basket includes a conical portion.

Still more particularly, the present invention provides a process vessel of the above-described type in which the screen basket has a low surface energy.

Yet more particularly, the present invention provides a process vessel of the above-described character in which the screen basket includes only a single major seam extending in the horizontal or vertical direction, and is free of ribs and other structure which could trap and retain microvessel cells.

Additionally, the present invention provides a process vessel as described above wherein the vessel includes a valving structure effective to separate microvessel cells from other materials present in the processing chamber, and in which the valving structure is configured to preserve and deliver a substantial portion of the microvessel cells yielded by the process vessel.

Yet more particularly, the present invention provides a process vessel of the described character in combination with a holder for the vessel and a canister which may enclose the holder and process vessel together to preserve the tissues under processing as well as protecting medical personnel from tissue and blood contact.

Additional objects and advantages of the present invention will be apparent from a reading of the following detailed description of an exemplary preferred embodiment of the invention taken in conjunction with the appended drawing Figures in which like reference numerals denote the same features or features which are analogous in structure.

DESCRIPTION OF THE DRAWING FIGURES

FIG. 1 provides an exploded perspective view of apparatus embodying the present invention;

Figure 4:
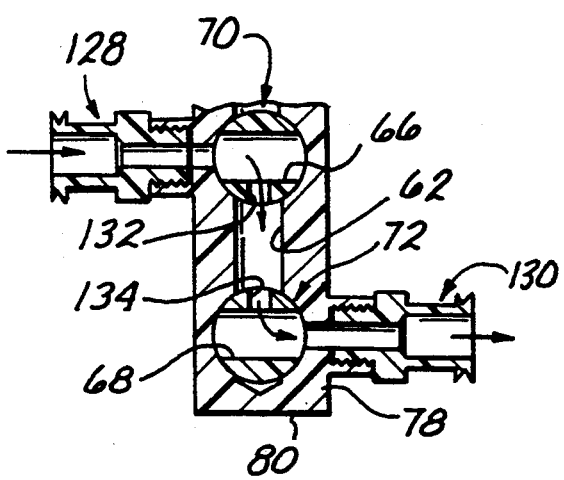
Figure 6:
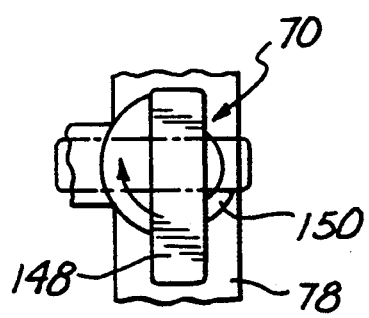
Figure 2:
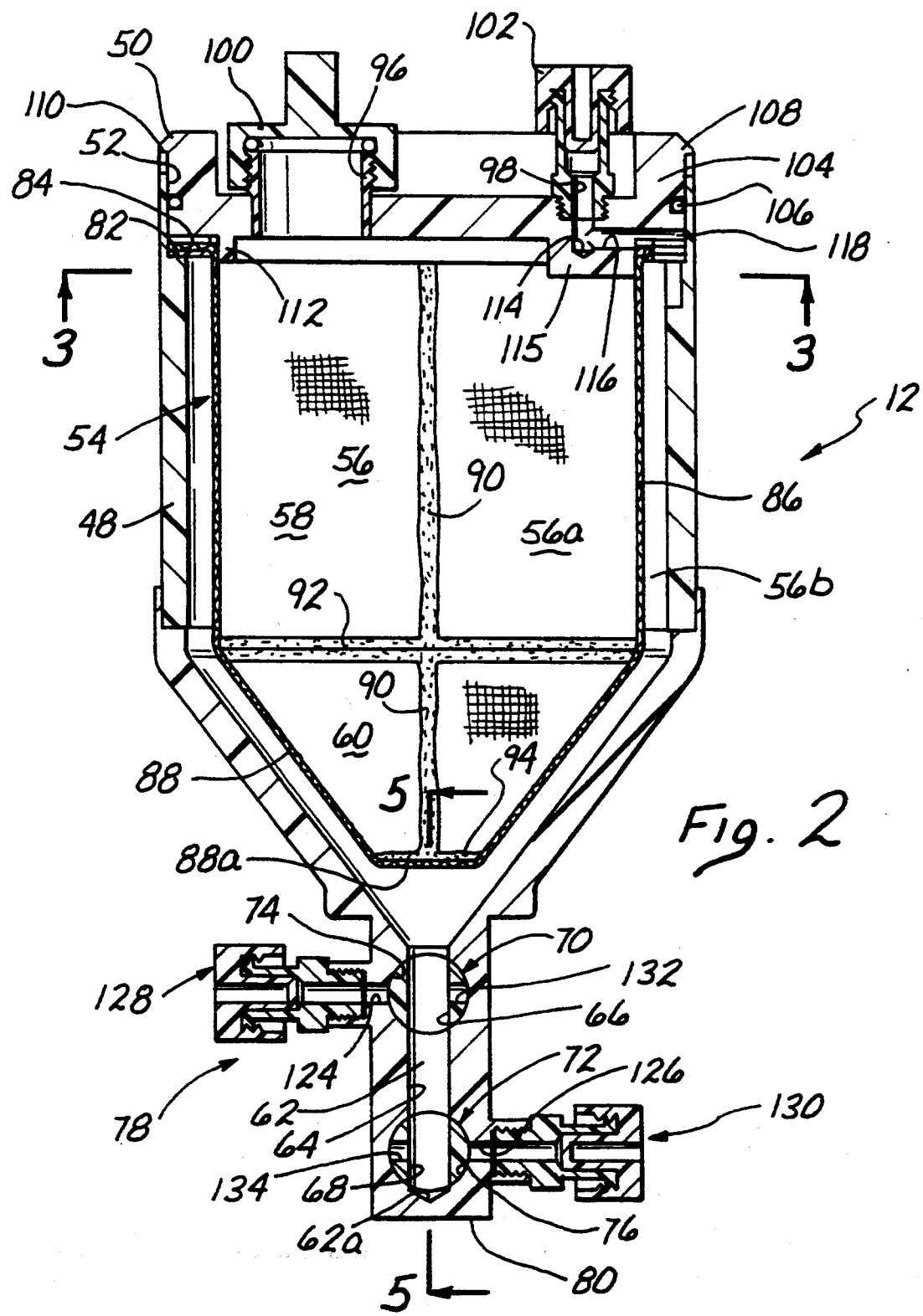
FIG. 2 is a cross sectional view at an enlarged scale of a component part of the apparatus depicted in FIG. 1.
Figure 5:
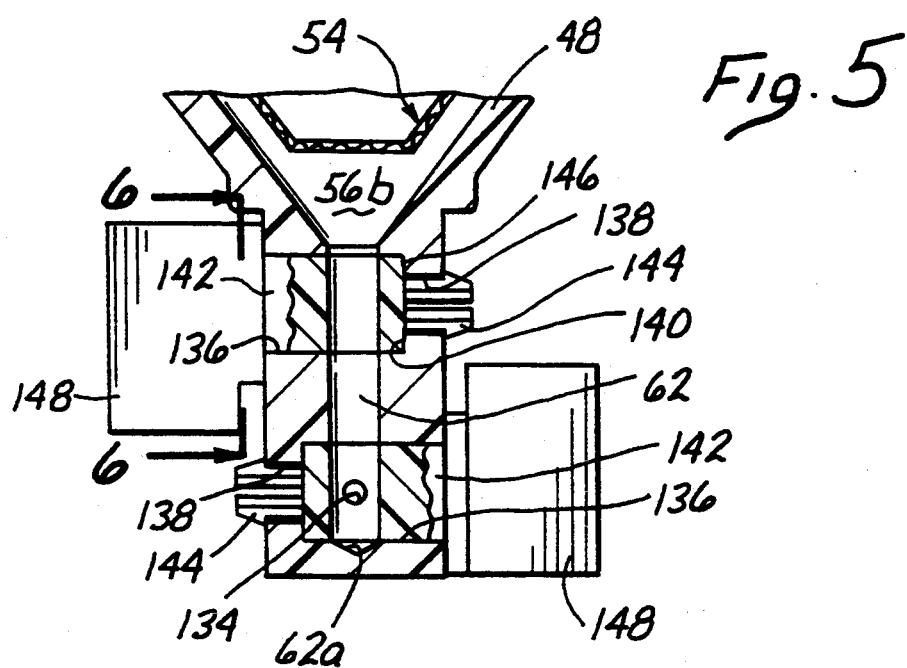

FIG. 4 provides a fragmentary cross sectional view of a part of the apparatus of FIG. 2 shown in an alternative operative position;

FIG. 5 provides a fragmentary cross sectional view taken along line 5—5 of FIG. 2; and FIG. 6 is a fragmentary exterior view of the apparatus depicted in FIG. 4, and shows the apparatus in alternative operative positions.

DETAILED DESCRIPTION OF THE PREFERRED EXEMPLARY EMBODIMENT

As those ordinarily skilled in the pertinent arts will appreciate, the current technology teaches to harvest tissue which is rich in microvessels, and to separate these microvessel cells from the tissue for lining a vascular graft which is then implanted into the patient who donated the tissue. This procedure provides a remarkably reduced thrombogenicity for the synthetic vascular grafts. The donated microvessel cells are recognized by the body of the patient as "self" so that initial acceptance of the graft into the patient's circulatory system without adverse reactions, as well as the construction of new vascular tissues on the graft are improved.

The present technology teaches to harvest adipose or fat tissues from the patient, and to digest these fat tissues with an enzyme to free the microvessel cells. The microvessel cells are then separated from the fat cells and are deposited on the inner lumenal surface of the vascular graft. Viewing FIG. 1, a processing vessel assembly 10 is shown in exploded view. This processing vessel assembly 10 includes a processing vessel 12, a holder 14 for the processing vessel 12, and a canister assembly 16 which receives the processing vessel 12 in the holder 14. The canister assembly 16 includes a bowl portion 18 and a lid portion 20. Within the bowl portion 18, a chamber 22 is defined which opens upwardly at 24. Around the opening 24 on the exterior of the bowl portion 18, a male thread 26 is defined which may threadably and substantially sealingly engage with an internal female thread (not shown) defined within a depending lip 28 of the lid portion 20.

In view of the above, it should be kept in mind that the processing vessel 12 may be supportingly received in the holder 14 and be substantially sealed within the canister assembly 16 for centrifuging and handling of the process vessel 12. In this way, any inadvertent spillage of tissues or fluids from within the process vessel is contained in the canister assembly 16, so that safety for medical personnel is improved by use of the present invention. Further, the canister assembly 16 helps to preserve the sterility of the process vessel 12 and its contents during handling and during the digestion and centrifuging operations. Also, the holder 14 includes a base part 30 in the form of a annular plate which may rest upon a laboratory table or bench. From the base part 30, four equally spaced apart arms 32 extend upwardly to support an annular ring 34. Above the annular ring part 34, each of the arms 32 defines a respective arcuate tab or handle portion 36. When the holder 14 is received into the chamber 22 of the bowl portion 18, the tabs 36 extend upwardly of the opening 24. Consequently, the holder 14 and processing vessel 12 may together be lifted out of the bowl portion 18.

Each of the arms 32 of the holder 14 includes a radially thinner portion 38 depending from the ring 34 to an angular shoulder 40. The processing vessel 12 is engageable with the angular shoulders 40 to be supported within the holder 14. Below the angular shoulders 40, each arm includes a radially thicker portion 42 extending downwardly to join with the base 30. Within the portions 42, the arms 32 cooperatively define a chamber or space 44 wherein a lower portion of the process vessel 12 is received, as will be further explained. Importantly, the base 30 defines an opening 46 through which a lower portion of the process vessel 12 extends to engage and be supported by a floor (not shown) of the bowl portion 18 of canister 14 during centrifuging of the process vessel assembly 10, as also will be explained.

Figure 1:
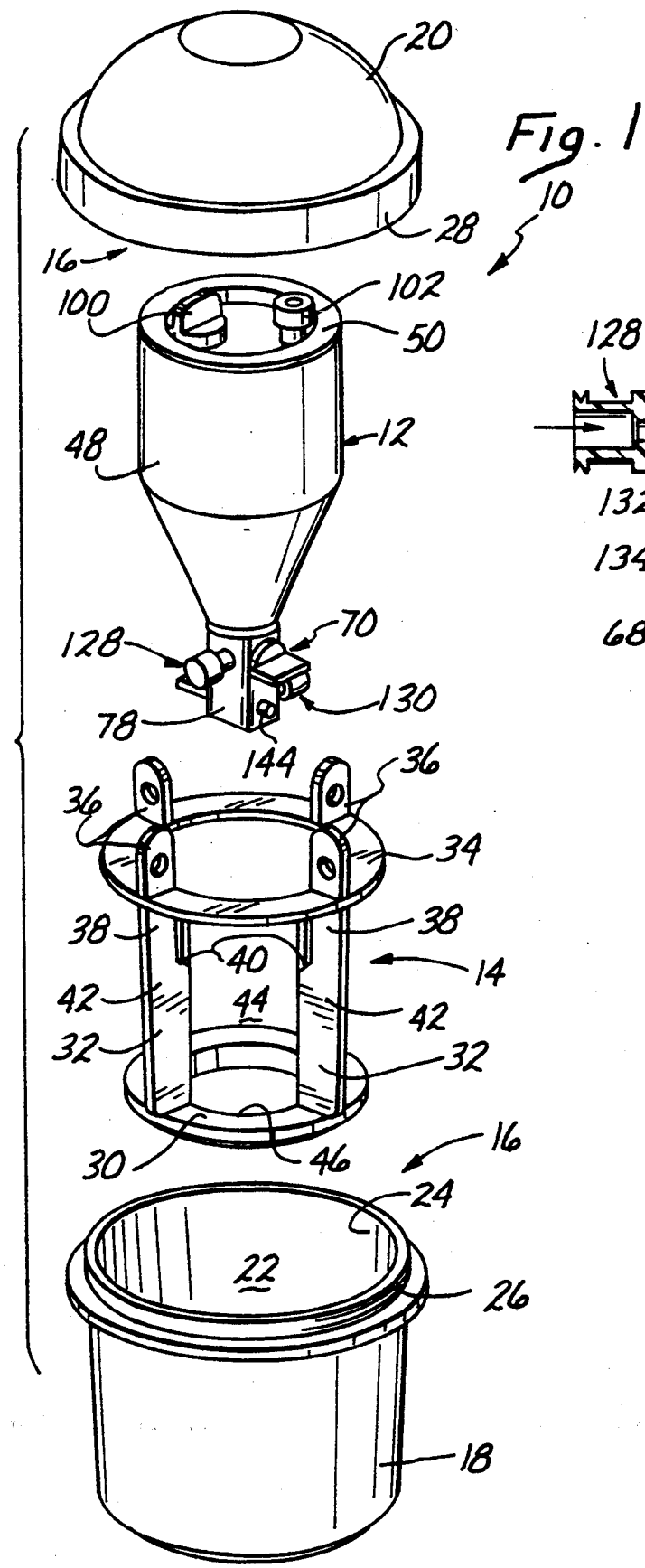
Figure 3:
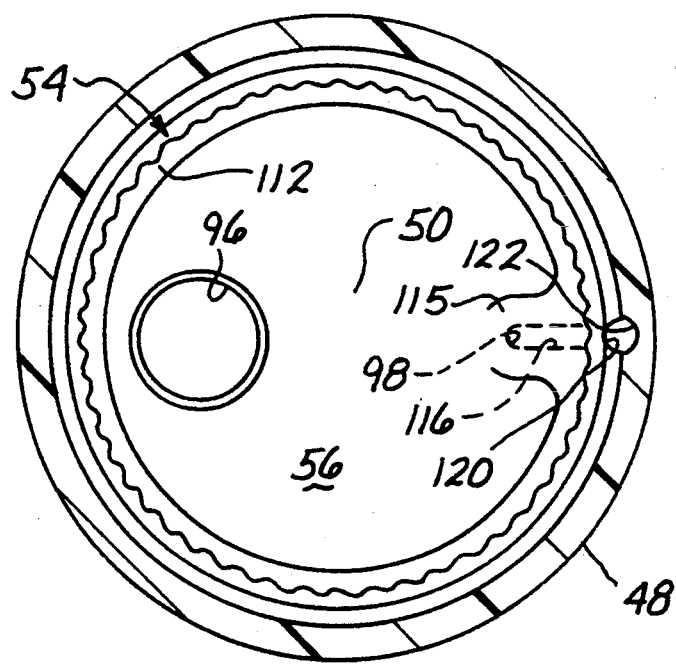
FIG. 3 is a cross sectional view taken at line 3—3 of FIG. 2, looking in the direction of the arrows.

Viewing now FIGS. 1, 2, and 3, in conjunction, it is seen that the process vessel 12 itself is an assembly including a chambered housing 48, a cap member 50 closing an opening 52 in the housing 48, and a screen basket assembly 54 captured within the chamber 56 of the housing 48 by the cap 50. More particularly, the chamber 56 includes a cylindrical upper portion 58 communicating downwardly to a conical lower portion 60. The conical lower portion 60 of the chamber 56 similarly communicates downwardly to a comparatively small diameter ampule chamber portion 62. As will be seen, the ampule chamber portion 62 is defined cooperatively by a bore 64 defined by the housing 48, and a pair of aligned bores 66 and 68 which are defined respectively by a pair of valving members 70 and 72, The valving members 70 and 72 are respectively received sealingly and rotatably in respective transverse bores 74 and 76 defined in a lower boss portion 78 of the housing 48. This lower boss portion 78 extends through the opening 46 of holder 14 and defines a lower surface 80 which is engageable with the canister bowl 18 to support the process vessel 12 in opposition to the loads which are created at centrifuging of several hundred G's, or higher. As will be seen, the valving members 70, 72 in cooperation with the housing 48 define a pair of two-way stop cocks.

Near its upper extent, the housing 48 includes an internal shoulder 82 upon which rests an upper radially outwardly extending flange portion 84 of the screen basket assembly 54. depending from the flange portion 84, the screen basket assembly 54 includes an upper cylindrical portion 86, and a lower conical portion 88. This lower conical portion 88 is truncated to define a horizontal end portion 88a, which is disposed congruent to and above the upper end of the bore 64 defining the lower ampule housing chamber portion 62.

Both the upper cylindrical portion and the lower conical portion 88 of the screen basket assembly 54 are spaced slightly away from the inner surfaces of the corresponding cylindrical 58 and conical 60 portions of the chamber 56. Consequently, the screen basket assembly divides the chamber 56 into an inner portion 56a, which is within the screen basket assembly, and an outer portion 56b, which lies between the outside of the screen basket assembly 54, and the inner surfaces of the housing 48 which define the chamber 56.

Preferably, the screen basket assembly 54 includes a flange portion 84 fabricated of a polymer material, such as polyethylene, polyester, or polypropylene. The screen basket itself is fabricated of polymer mesh material. Preferably, this polymer mesh material is polyester screen of about 20 to 800 micron mesh size. More particularly, the polyester mesh screen material is of mesh size in the range of from 200 microns to about 500 microns. Most preferably, the mesh size of the screen material is about 350 microns, and the material has about a 50 percent open area. A material of this type which has been successfully used in the practice of the present invention is available from Tetko Incorporated, of Briar Cliff Manor, N.Y., and is available as a square or twill weave material. Square weave material has been successfully used to practice the present invention. Alternatively, polymer screen materials of polyethylene, polypropylene, nylon, fluoropolymers, and other materials of low surface energy and good biocompatability may be used to practice the present invention. By low surface energy is meant that the materials have a low electro-chemical energy in comparison with metals. As is pointed out herein, the use of metallic screens to hold fat tissue for rinsing has itself been shown to be detrimental to the yield of viable microvessel cells.

Considering for the moment FIGS. 2 and 3, it will be seen that the screen basket assembly 54 includes only a single major vertical seam 90 in each of the cylindrical and conical portions 86, and 88. Similarly, the screen basket assembly 54 includes only a single major horizontal seam 92 at the juncture or the cylindrical and conical portions 86, and 88. The small horizontal seam 94, which is defined at the juncture of the conical portion 88, and the conical truncation portion 88a, is of comparatively small size so as not to compromise the design integrity of the screen basket assembly 54, as will be appreciated after a complete reading of the following functional description of the process vessel 12. Preferably, the seams 90, 92, 94 are made by heat melting or ultrasonic welding. That is, the screen basket 54 is substantially free of reinforcing ribs, folds, seams, reinforcing rods, or tie bolt-like features. These features might support the basket for centrifuging, or join together panels or parts of the screen material to form the basket, but they also serve to trap or retain microvessel cells, and lower the cell yield of the process and apparatus.

Considering FIGS. 2 and 3 further, it is seen that the cap 50 closes the opening 52, and defines a pair of ports 96, and 98. The port 96 communicates with the interior chamber 56a of the screen basket, while the port 98 communicates with the exterior space 56b between the outside of the screen basket 54 and the housing 48, as will be further explained. Each of the ports 96 and 98 is provided with a respective removable and resealable closure member 100 and 102. Also, the cap 50 includes a cylindrical portion 104 which is received in the opening 52 of the housing 48. This cylindrical portion 104 carries an O-ring type of sealing member 106 which sealingly cooperates with the housing 48 to sealingly dispose the cap 50 in the opening 52. Above the cylindrical portion 104, the cap 50 also includes a small radially outwardly extending rim 108. This rim engages the upper edge 110 of the housing 48 to position the cap in the opening 52 of the housing 48.

Circumscribing the ports 96 and 98, the cap 50 includes a depending ring portion 112 which engages inside of the flange 84 of the screen basket assembly 54 to maintain this flange in engagement with the shoulder 82. As FIG. 2 shows, the port 98 leads to an end wall portion 114, However, FIG. 3 shows that cap member 50 internally defines a boss 115 below the port 98 and joining with the ring portion 112. A small passage 116 extends outwardly from the port 98 through the boss 115 and communicates with a groove 118 extending across the flange 84 above the space 56b. FIG. 3 also shows that the flange 84 defines an arcuate notch 120 congruent with an oppositely disposed arcuate notch 122 in and below the shoulder 82. Consequently, the port 98 is communicated with the space 56b in chamber 56 outwardly of the screen basket assembly 54.

FIG. 2 illustrates that the boss 78 defines a pair of comparatively small bores 124, 126 respectively communicating outwardly from the bores 74, 76 to corresponding external bosses 128, and 130, each of which defines a luer type of fitting. This drawing figure also shows that each of the valving members 70, and 72 likewise defines a respective passage 132, 134 communicating with the through bores 66, 68. In FIG. 4, it is seen that the valving members 70 and 72 are rotatable in the housing 48 to communicate each of the through bores 66 and 68 with the luer fittings 128 and 130, and to communicate the passages 132 and 134 with the bore 64 between the transverse bores 74 and 76 which receive the valving members 70 and 72. Consequently, the ampule chamber portion 62 is isolated from the chamber 56, and a lower small chamber portion 62a is isolated from the remainder of the ampule chamber portion. The ampule chamber portion 62 is communicated with the luer fittings 128 and 130.

FIG. 5 depicts that the bores 74 and 76 are stepped to define a first larger diameter portion 136 and a second smaller diameter portion 138. Intermediate of the bore portions, the housing 48 defines a step 140 on each of the bores 74 and 76. The valving members 70 and 72 are similarly stepped to include a larger diameter cylindrical portion 142, and a smaller diameter barb portion 144. The barb portion 144 is received through the bore portion 138 so that shoulders 146 on the valving members 70 and 72 engages the steps 140 on these bores. Outwardly of the boss portion 78 of the housing 48, the valving members 70 and 72 each include a blade-like handle portion 148. As can be seen in the fragmentary illustration of FIG. 6, the boss 78 includes an arcuate stop feature 150 which at its opposite ends is engaged by the handle portion 148 to define the two alternative operative positions for the valving members 70 and 72. Boss 78 has a respective stop feature 150 for each of these valving members.

Having considered the structure of the process vessel assembly 10, attention may now be directed to its use and function. As those ordinarily skilled in the pertinent arts will know, adipose or fat tissue, which is rich in microvessel cells, is harvested from a patient who is to receive a synthetic vascular graft by use of a liposuction apparatus (not shown). The harvested fat tissue immediately from the body and while still warm is injected into the chamber 56a of the process vessel 12 via the port 96 so that this tissue resides within the screen basket assembly 54.

Importantly, the Applicants have determined that the effectiveness with which this fat tissue is washed or rinsed to remove lysed fat cells, blood cells, and liquid fat, for example, has a very marked effect on the yield of microvessel cells which may be recovered from the fat tissues. Consequently, the chamber 56a has a volume of about 150 cc, while the volume of fat tissue usually harvested is from 50 cc to 100 cc. As a result, there is provided a considerably ullage space or agitation space within the chamber 56a.

Rinsing solution which is warmed to body temperature may be introduced into the chamber 56 via the port 96, the port closed, and the process vessel 12 agitated to separate the liquid fat and other undesired materials from the fat tissues. Importantly, the screen basket 54 almost completely fills the chamber 56 so that there is no significant void volume in which undesired materials may collect or be hidden from an effective rinsing operation. That is, the volume of chamber 56a within the screen basket 54 is substantially equal in significant effect to the volume of the entire chamber 56 in the housing 48. No ullage volume exists which is shielded or hidden from an effective rinsing by the fat tissues or by structure within the chamber 56.

In order to remove the rinsing solution from the chamber 56, the vessel 12 is tipped toward the port 98 and a syringe is inserted into this port to aspirate the rinsing solution along with the liquid fat and other undesired materials. By repeated introduction of rinsing solution, agitation, and aspiration of the rinse solution along with the undesired materials, a very effective cleansing of the fat tissues in screen basket 54 is effected. During this rinsing operation, the process vessel 12 will reside in its holder to better facilitate handling of the vessel and virtually eliminate chances of the vessel being spilled.

Next, an enzymatic digesting material, such as collagenase, which is also warmed to body temperature is introduced into the chamber 56. The process vessel 12, which is already in its holder 14 from the rinsing operation, is placed into the chamber 22 of the canister 16, and this canister is closed with lid 20. This process vessel assembly with the rinsed fat tissues and enzymatic digestion material is placed into a warm air oven provided with an agitation plate. The warm air oven serves to preserve the tissues at about body temperature or higher and to facilitate digestion with the enzymatic material to free the microvessel cells. This digestion and freeing of the microvessel cells is assisted by the agitation.

Directly from the air and agitation oven, the process vessel assembly 10 is transferred to a centrifuge. Again at this stage of the process, the holder 14 and closed canister 16 serve to prevent spilling of the contents of the process vessel 12, and to protect medical personnel from contact with patient tissues and fluids. The centrifuge is operated at about 700 G's for a time sufficient to separate the freed microvessel cells from the fat cells in the chamber 56. During this centrifuging operation, the valving members 70 and 72 are in the positions depicted by FIGS. 2 and 5. Consequently, a "pellet" of microvessel cells is formed in the ampule chamber portion 62 consisting of the portion of bore 64 between the valving members 70, and 72, as well as the bores 66 and 68 of these valving members. A small residue of packed red blood cells and other solid debris is left in the chamber portion 62a.

After the process vessel assembly 10 is removed from the centrifuge, the vessel 12 in its holder 14 is removed from the canister 16, and placed in association with a cell deposition device containing the synthetic graft which the patient is to receive. In order to transfer the pellet of microvessel cells from the ampule chamber portion 62 of the chamber 56 to the cell deposition device, a source of sterile buffered liquid is connected to the luer fitting 128, while the luer fitting 130 is connected to the cell deposition device, and the valving members 70 and 72 are rotated to their positions shown in FIG. 4. Additionally, the cell deposition device may be evacuated so that a partial vacuum assists in pulling liquid from the source into fitting 128, through the bore 66, through the passage 132 to the bore 64, and through passage 134 to bore 68 of valving member 72. Consequently, the liquid and pellet of microvessel cells is communicated to the cell deposition device. Importantly, the bores 66 and 68 of valving members 70 and 72 define part of the ampule chamber in which microvessel cells are collected by the centrifuging operation described above. The microvessel cells which are collected in these bores are preserved as part of the pellet of cells by the design of the present stop cock valve structures, and is communicated to the cell deposition device. Also importantly, the sterile liquid which is introduced by luer fitting 128 flows through the bores 66 and 68 to flush substantially all of the collected microvessel cells from these bores to the cell deposition device.

Construction and testing of actual process vessel assemblies 10 and of process vessels 12 in accord with the present invention has shown a remarkable improvement in the yield of microvessel cells per gram of fat tissue processed. In fact, the yield of microvessel cells produced by the apparatus and method of the present invention was substantially twice that of conventional technology in all cases, and in some cases was close to, or more than, an order of magnitude above the yield from conventional technology devices with the same fat tissues. Consequently, the reduction in thrombogenicity of a synthetic graft which can be effected by lining the graft with microvessel cells from the patient can be improved by use of the present invention. Also, the efficacious number of microvessel cells necessary to treat the synthetic graft may be obtained with a smaller extraction of adipose tissue from the patient.

Additionally, the process vessel 12 of the present invention is considerably less expensive to manufacture than the conventional devices because it can be injection molded. Particularly, the section thickness of the walls which define the chamber 56 are made sufficiently thin that they can easily be injection molded while having sufficient strength. Also, the holder 14 may be injection molded. Also, the boss 78 which defines ampule chamber portion 62 is sufficiently thin in section to be injection molded.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. A process vessel for use in receiving, cleansing, digesting and isolating certain identifiable cells from tissues, said process vessel comprising:
   a housing defining a process chamber, said process chamber including a lower conical portion; and
   a screen basket including a conical portion defining a lower part of said screen basket, said screen basket and its conical portion positioned in said process chamber and its lower conical portion to define a gap separating said screen basket from said housing, the size of said gap being substantially consistent across the screen basket and its conical portion.

2. The process vessel of claim 1 in which said screen basket has a low surface energy when compared with metals.

3. The process vessel of claim 2 in which said screen basket is fabricated of a polymer material.

4. The process vessel of claim 3 in which said polymer material is chosen from the group consisting of polyethylene, polypropylene, polyester, nylon, and fluoropolymers.

5. The process vessel of claim 4 in which said screen basket has a mesh in which the size of its openings is in the 20 micron to 800 micron range.

6. The process vessel of claim 5 wherein said screen basket has a mesh in which the size of its openings is in the 200 micron to 500 micron range.

7. The process vessel of claim 5 in which said screen basket has a mesh in which the size of its openings is about 350 microns.

8. The process vessel of claim 3 in which said polymer material of said screen basket has an open area of about 50 percent.

9. The process vessel of claim 1 in which said gap defines a portion of said process chamber outwardly of said screen basket, said housing defining a port which fluidly communicates with said chamber portion without fluid flow through said screen basket.

10. The process vessel of claim 9 in which said housing includes a cap portion, said cap portion defining said port, and a passage communicating from said port to said chamber portion outwardly of said screen basket.

11. The process vessel of claim 10 in which said cap portion further defines a second port opening into the interior of said screen basket.

12. The process vessel of claim 1 wherein said housing further includes an ampule passage portion of said chamber which opens downwardly from the lower conical portion of said chamber, said housing further including a pair of vertically spaced apart valving devices which each include a respective bore defining a portion of said ampule passage portion in a first position for said valving devices.

13. The process vessel of claim 12 wherein said pair of valving devices also each include a transverse passage defining a T-intersection with said respective bore of the valving device in a second position of said valving devices, said respective bores being disposed out of communication with said ampule passage portion of said chamber and in communication with a respective fitting opening outwardly on said housing, said transverse passages of each valving device respectively communicating in said second position thereof with a portion of said ampule passage portion between said vertically spaced apart valving devices to communicate said respective fittings with one another via said ampule passage portion of said chamber.

14. The process vessel of claim 12 wherein one of said pair of valving devices includes a valving member rotatably received sealingly in said housing, said housing defining a stepped bore receiving said valving member, and said valving member including a cylindrical portion sealingly received in said stepped bore and defining said bore for said valving device and said ampule passage portion of said chamber intersecting therewith.

15. The process vessel of claim 14 wherein said housing includes a shoulder adjacent to said stepped bore, said valving member including a barb portion engaging said shoulder to retain said valving member sealingly in said stepped bore.

16. The process vessel of claim 1, and a canister for receiving and sealingly enclosing said process vessel.

17. The process vessel of claim 16, and a holder configured to be received into said canister along with said process vessel to support the latter in a vertical orientation within said canister.

18. The process vessel of claim 1 wherein said tissues are adipose fat tissues, and said identifiable cells are microvessel cells.

19. A process vessel assembly for separating and concentrating microvessel cells from fat tissue harvested from a human donor preparatory to use of said microvessel cells to coat an inner luminal surface of a graft to be implanted in said human donor, said process vessel assembly including:
(a) a process vessel canister including both a bowl-like portion defining a chamber and an upper opening to said chamber, and a lid portion sealingly engageable with said bowl-like portion to span and close said opening;
(b) a process vessel for receiving, cleansing, digesting, and centrifuging said fat tissue to separate and concentrate said microvessel cells, said process vessel being receivable into said chamber of said process vessel canister, said process vessel comprising:
(i) a housing defining a process chamber, said process chamber including a lower conical portion; and
(ii) a screen basket including a conical portion defining a lower part of said screen basket, said screen basket and its conical portion positioned in said process chamber and its lower conical portion to define a gap separating said screen basket from said housing, the size of said gap being substantially consistent across the screen basket and its conical portion; and
(c) a holder for supporting said process vessel in a vertical position both on a horizontal support surface and in said process vessel canister, said holder engaging said bowl-like portion to limit movement of said process vessel in said chamber during centrifuging of said process vessel assembly to separate and concentrate said microvessel cells from said fat tissue.

20. The process vessel assembly of claim 19 wherein said process chamber includes an upper cylindrical portion and an ampule passage portion descending from said lower conical portion; and wherein said screen basket further includes an upper cylindrical portion.

21. The process vessel assembly of claim 20 wherein said screen basket is made of mesh material in which the size of its openings range from 20 to 800 microns.

22. The process vessel assembly of claim 21 wherein said screen basket is made of mesh material in which the size of its openings range from 200 to 500 microns.

23. The process vessel assembly of claim 22 wherein said screen basket is made of mesh material in which the size of its openings is about 350 microns.

24. The process vessel assembly of claim 23 wherein said screen basket is made of mesh material fabricated of polymer material.

25. The process vessel assembly of claim 24 wherein said polymer material is selected from the group consisting of polyester, polypropylene, polyethylene, nylon, and fluoropolymers.

26. The process vessel assembly of claim 20 wherein said screen basket is free of reinforcing ribs and includes substantially only a single horizontal or vertical seam, whereby microvessel cells separated by digestion from said fat tissue are not significantly trapped or retained on reinforcing ribs or seams of said screen basket.

27. The process vessel assembly of claim 26 wherein said screen basket includes only a single horizontal seam between said cylindrical and said conical portions and a single vertical seam.

28. The process vessel assembly of claim 20 wherein said housing further includes a pair of vertically spaced apart valving devices which each include a respective bore defining a portion of said ampule passage portion of said chamber in a first position for said valving devices.

29. The process vessel assembly of claim 28 wherein said pair of valving devices also each include a transverse passage defining a T-intersection with said respective bore of the valving device in a second position of said valving devices, said respective bores being disposed out of communication with said ampule passage portion of said chamber and in communication with a respective fitting opening outwardly on said housing, said transverse passages of each valving device respectively communicating in said second position thereof with a portion of said ampule passage portion between said vertically spaced apart valving devices to communicate said respective fittings with one another via said ampule passage portion of said chamber.

30. The process vessel assembly of claim 29 wherein one of said pair of valving devices includes a valving member rotatably received sealingly in said housing, said housing defining a stepped bore receiving said valving member, and said valving member including a cylindrical portion sealingly received in said stepped bore and defining said bore for said valving device and said ampule passage portion of said chamber intersecting therewith.

31. The process vessel assembly of claim 30 wherein said housing includes a shoulder adjacent to said stepped bore, said valving member including a barb portion engaging said shoulder to retain said valving member sealingly in said stepped bore.

* * * * *